(12) United States Patent
Iida et al.

(10) Patent No.: US 6,713,225 B2
(45) Date of Patent: Mar. 30, 2004

(54) 1,2-NAPHTHOQUINONE-2-DIAZIDESULFONATE ESTER PHOTOSENSITIVE AGENT, METHOD FOR PRODUCING THE PHOTOSENSITIVE AGENT, AND PHOTORESIST COMPOSITION

(75) Inventors: Hirotada Iida, Ichikawa (JP); Miharu Suwa, Ichikawa (JP); Yuichi Hagiwara, Ichikawa (JP); Katsumi Tada, Katori-gun (JP); Suehiro Katori, Katori-gun (JP); Tsuneaki Miyazaki, Inba-gun (JP)

(73) Assignee: Toyo Gosei Kogyo Co., Ltd., Chiba (JP)

( * ) Notice: Subject to any disclaimer, the term of this patent is extended or adjusted under 35 U.S.C. 154(b) by 0 days.

(21) Appl. No.: 10/386,215

(22) Filed: Mar. 11, 2003

(65) Prior Publication Data

US 2003/0175613 A1 Sep. 18, 2003

(30) Foreign Application Priority Data

| Mar. 15, 2002 | (JP) | 2002-072437 |
| Dec. 27, 2002 | (JP) | 2002-381849 |
| Dec. 27, 2002 | (JP) | 2002-381850 |

(51) Int. Cl.[7] ............ G03F 7/023; G03F 7/30; C07C 303/28
(52) U.S. Cl. ............ 430/192; 430/165; 430/191; 430/193; 534/557
(58) Field of Search ............ 430/192, 191, 430/193, 165; 534/557

(56) References Cited

U.S. PATENT DOCUMENTS

| 5,635,328 A | * | 6/1997 | Higashino et al. | 430/166 |
| 5,677,101 A | * | 10/1997 | Noguchi et al. | 430/166 |
| 5,723,253 A | * | 3/1998 | Higashino et al. | 430/166 |
| 5,792,585 A | * | 8/1998 | Ida et al. | 430/191 |
| 6,015,649 A | * | 1/2000 | Mori | 430/193 |
| 6,197,473 B1 | * | 3/2001 | Kihara et al. | 430/192 |

FOREIGN PATENT DOCUMENTS

| JP | 6167805 | 3/1979 |
| JP | 7120917 | 8/1981 |
| JP | 1189644 | 6/1982 |
| JP | 62153950 | 11/1990 |
| JP | 3279957 | 7/1991 |
| JP | 9077736 | 11/1992 |
| JP | 207291 | 3/2002 |
| WO | 9007538 | 7/1990 |

OTHER PUBLICATIONS

Deforest, W.S., *Photoresist*. McGraw–Hill Book Company (1975), pp. 48–55.
Hoberg, A.G. Sverker, *J. Org. Chem.* (1980), vol. 45, pp. 4498–4500.
Aoyama, Y., *J. Am. Chem. Soc.* (1989), vol. 111, pp. 5397–5404.

* cited by examiner

*Primary Examiner*—John S. Chu
(74) *Attorney, Agent, or Firm*—Huntley & Associates, LLC

(57) ABSTRACT

The invention provides a 1,2-naphthoquinone-2-diazidesulfonate ester photosensitive agent which is useful as a photosensitive agent employed in a photoresist for producing semiconductor integrated circuits, liquid crystal displays, EL displays, etc., a method for producing the photosensitive agent, and a photoresist composition containing the photosensitive agent. The 1,2-naphthoquinone-2-diazidesulfonate ester photosensitive agent is produced by reacting a polyhydric phenol with 1,2-naphthoquinone-2-diazidesulfonyl chloride in the presence of a neutralizing agent, wherein the polyhydric phenol is obtained by a condensation reaction between resorcinol and at least one aldehyde selected from C3–C10 aldehydes, and contains, as a predominant component, a compound represented by formula (I) and components exhibiting a retention time as measured by using GPC shorter than that of the compound represented by formula (I) in an amount of 10% or less:

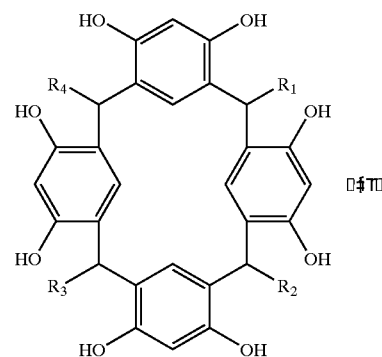

wherein each of $R_1$, $R_2$, $R_3$, and $R_4$ represents a C2–C9 alkyl group.

8 Claims, 1 Drawing Sheet

1,2-NAPHTHOQUINONE-2-DIAZIDESULFONATE ESTER PHOTOSENSITIVE AGENT, METHOD FOR PRODUCING THE PHOTOSENSITIVE AGENT, AND PHOTORESIST COMPOSITION

BACKGROUND OF THE INVENTION

1. Field of the Invention

The present invention relates to a 1,2-naphthoquinone-2-diazidesulfonate ester photosensitive agent, a method for producing the photosensitive agent, and a photoresist composition. More particularly, the present invention relates to a 1,2-naphthoquinone-2-diazidesulfonate ester photosensitive agent which has high solubility in solvent and is a useful photosensitive agent for a photoresist used for producing semiconductor integrated circuits, liquid crystal displays, etc., a method for producing the photosensitive agent, and photoresist composition containing the photosensitive agent.

2. Description of the Related Art photosensitive agents containing a 1,2-naphthoquinone-2-diazidesulfonate ester are generally used in positive-type photoresists as a photosensitive component, in combination with an alkali-soluble binder resin such as a novolak resin. The positive-type photoresists, having high resolution, are used for producing semiconductor integrated circuits, liquid crystal displays, EL displays, etc.

Generally, the 1,2-naphthoquinone-2-diazidesulfonate ester photosensitive agent serving as a photosensitive component of such positive-type photoresists is produced by reacting a polyphenolic compound and 1,2-naphthoquinone-2-diazidesulfonyl chloride in the presence of a neutralizing agent. Polyphenolic compounds known to be used in the above reaction include polyhydroxybenzophenones (W. S. Deforest, "Photoresist," McGraw-Hill Book Company, 1975, p. 48–55 and Japanese Patent Application Laid-Open (kokai) No. 62-153950); polyhydroxytriphenylmethanes (Japanese Patent Application Laid-Open (kokai) No. 1-189644); and polyphenolic compounds, each being formed by linking 3, 4, or 5 phenol molecules with methylene (WO90/07538 and Japanese Patent Application Laid-Open (kokai) Nos. 6-167805 and 7-120917). 1,2-Naphthoquinone-2-diazidesulfonate esters can be produced at low cost from polyhydroxybenzophenone, inter alia, trihydroxybenzophenone and tetrahydroxybenzophenone. Therefore, 1,2-naphthoquinone-2-diazidesulfonate esters are employed as a photoseisitive component of a photoresist for producing semiconductor integrated circuits and liquid crystal display.

Polyhydroxybenzophenones show a high absorption at i-line (365 nm), and a photoresist containing a polyhydroxybenzophenone provides a poor pattern form through exposure to i-line. Thus, such a photoresist is employed for exposure to g-line (436 nm). Photoresists employed for exposure to i-line generally contain polyhydroxytriphenylmethanes or polyphenolic compounds formed by linking 3, 4, or 5 phenol molecules with methylene. However, production of such polyphenolic compounds involves cumbersome steps, and the thus-produced polyphenolic compound has poor solubility in a resist solvent. Thus, a photoresist composition containing the polyphenolic compound raises problems; i.e., the composition may fail to attain sufficient dissolution of the photosensitive agent and possibly form unfavorable precipitates with the elapse of time.

Japanese Patent Application Laid-Open (kokai) No. 3-279957 discloses a 1,2-naphthoquinone-2-diazidesulfonate ester produced from a polyhydroxy compound, which is a cyclic polyphenolic compound that does not show an absorption at i-line and can be produced through an easy process. However, such a 1,2-naphthoquinone-2-diazidesulfonate ester produced from a cyclic polyhydroxy compound has also poor solubility in a resist solvent, and a photoresist composition containing the ester raises problems; i.e., the composition may fail to attain sufficient dissolution of the photosensitive agent and possibly form unfavorable precipitates with the elapse of time.

As described above, a variety of polyphenolic compounds and 1,2-naphthoquinone-2-diazidesulfonate ester photosensitive agents derived from the polyphenolic compounds are disclosed. However, there has not been known a 1,2-naphthoquinone-2-diazidesulfonate ester photosensitive agent having high solubility in a resist solvent, which ester is derived from a polyhydric phenol that does not show an absorption at i-line and can be produced through a simple process.

SUMMARY OF THE INVENTION

In order to solve the aforementioned problems, the present inventors have carried out extensive studies on 1,2-naphthoquinone-2-diazidesulfonate ester photosensitive agents produced from a cyclic polyhydroxy compound disclosed in Japanese Patent Application Laid-Open (kokai) No. 3-279957, which does not show an absorption at i-line and is easily produced; and have found that a specific 1,2-naphthoquinone-2-diazidesulfonate ester photosensitive agent obtained from a polyhydric phenol; i.e., a cyclic polyhydroxy compound produced through condensation of resorcinol and at least one aldehyde selected from C3–C10 aldehydes and containing higher-molecular-weight components in an amount below a certain level, has high solubility in a medium such as resist solvent, and that a photoresist composition containing the photosensitive agent exhibits satisfactory sensitivity and excellent storage stability and serves as a highly useful composition. The present invention has been accomplished on the basis of these findings.

Thus, an object of the present invention is to provide a 1,2-naphthoquinone-2-diazidesulfonate ester photosensitive agent which is useful as a photosensitive agent employed in a photoresist for producing semiconductor integrated circuits, liquid crystal displays, EL displays, etc. Another object of the invention is to provide a method for producing the photosensitive agent. Still another object of the invention is to provide a photoresist composition containing the photosensitive agent.

Accordingly, in a first aspect of the present invention, there is provided a 1,2-Naphthoquinone-2-diazidesulfonate ester photosensitive agent which is produced by reacting a polyhydric phenol(polyphenol) with 1,2-naphthoquinone-2-diazidesulfonyl chloride in the presence of a neutralizing agent, wherein the polyhydric phenol is obtained by a condensation reaction between resorcinol and at least one aldehyde selected from C3–C10 aldehydes, and contains, as a predominant component, a compound represented by formula (I) and components exhibiting a retention time as measured by using GPC shorter than that of the compound represented by formula (I) in an amount of 10% or less:

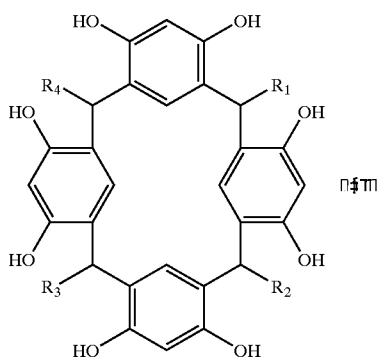

wherein each of $R_1$, $R_2$, $R_3$, and $R_4$ represents a C2–C9 alkyl group.

The polyhydric phenol containing the compound represented by formula (I) as a predominant component may contain, in an amount of 5% or less, components exhibiting a retention time as measured by using GPC shorter than that of the compound represented by formula (I).

Each of $R_1$, $R_2$, $R_3$, and $R_4$ in formula (I) may be a C4–C6 alkyl group.

The polyhydric phenol containing the compound represented by formula (I) as a predominant component may be reacted with 1,2-naphthoquinone-2-diazidesulfonyl chloride in an amount of at least 3 mol based on 1 mol of the polyhydric phenol.

The 1,2-naphthoquinone-2-diazidesulfonate ester photosensitive agent may be incorporated into a photoresist for exposure to i-line.

In a second aspect of the present invention, there is provided a photoresist composition comprising any of the aforementioned 1,2-naphthoquinone-2-diazidesulfonate ester photosensitive agent and an alkali-soluble resin.

The photoresist composition may be employed for exposure to i-line.

In a third aspect of the present invention, there is provided a method for producing a 1,2-naphthoquinone-2-diazidesulfonate ester photosensitive agent comprising the steps of: obtaining a polyhydric phenol by a condensation reaction between resorcinol and at least one aldehyde selected from C3–C10 aldehydes, which the polyhydric phenol contains, as a predominant component, the compound represented by formula (I), and components exhibiting a retention time as measured by using GPC shorter than that of the compound represented by formula (I) in an amount of 10% or less:

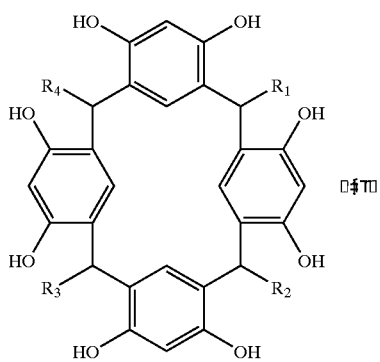

wherein each of $R_1$, $R_2$, $R_3$, and $R_4$ represents a C2–C9 alkyl group; and reacting the polyhydric phenol with 1,2-naphthoquinone-2-diazidesulfonyl chloride in the presence of a neutralizing agent.

The 1,2-naphthoquinone-2-diazidesulfonate ester photosensitive agent according to the present invention, which is derived from a polyhydric phenol predominantly containing a cyclic compound represented by formula (I), exhibits high solubility in solvent and can be produced, through an easy process, at low cost and on a large scale. The photoresist composition containing the photosensitive agent exhibits satisfactory sensitivity suitable for producing semiconductor integrated circuits, liquid crystal displays, EL displays, etc. through ultra-fine photolithography, as well as excellent storage stability, finding remarkable utility in practice. In particular, the photoresist composition is usefully employed for exposure to i-line.

DETAILED DESCRIPTION OF PREFERRED EMBODIMENTS

Figure 1:
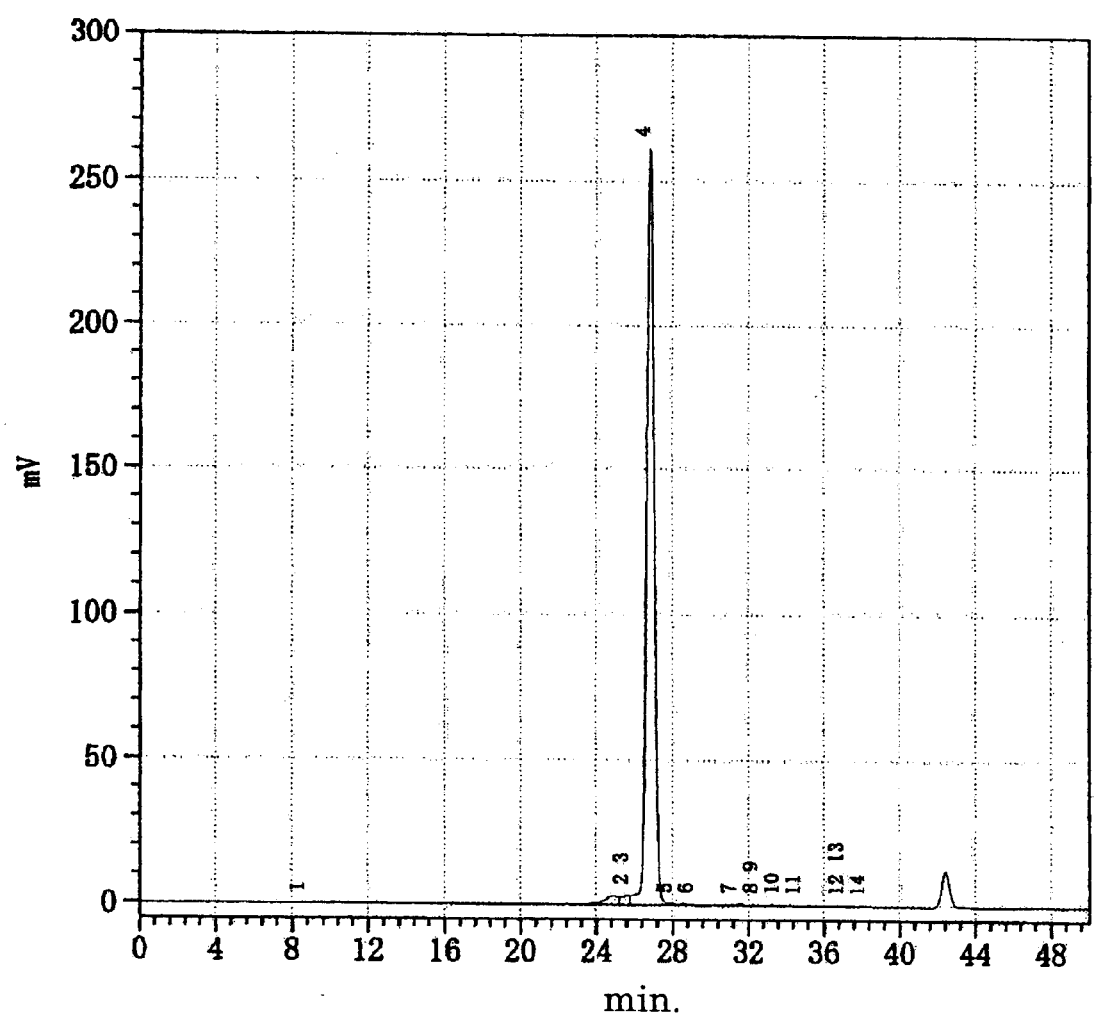
FIG. 1 is a GPC chart of the polyhydric phenol synthesized in Synthesis Example 1.

The present invention will next be described in more detail.

The 1,2-naphthoquinone-2-diazidesulfonate ester photosensitive agent of the present invention can be produced by reacting the polyhydric phenol that contains a compound represented by formula (I) as a predominant component with 1,2-naphthoquinone-2-diazidesulfonyl chloride in the presence of a neutralizing agent. The polyhydric phenol is obtained by a condensation reaction between resorcinol and at least one aldehyde selected from C3–C10 aldehydes. Here, in the present invention, the polyhydric phenol is a mixture comprising the compound represented by formula (I), which may contain isomers, and components exhibiting a retention time as measured by using GPC shorter than that of the compound represented by formula (I).

The compound represented by formula (I) is a compound formed through condensation of 4 mol of resorcinol and 4 mol of aldehyde so as to form a ring structure. The method for synthesizing the compound is disclosed in detail in, for example, A. G. Sverker Hoberg (J. Org. Chem., vol. 45, 4498 (1980)); and Y. Aoyama, et al. (J. Am. Chem. Soc., vol. 111, 5397 (1989)). When any of the above disclosed methods is employed, the target compound is readily synthesized. However, the method involves very cumbersome post treatment steps performed after reaction of resorcinol and aldehyde; e.g., further derivation of the product to another phenol derivative; purification; and re-transformation to the target phenol compound. Thus, the method is not preferably employed.

A preferred synthesis procedure will next be described.

Firstly, resorcinol and aldehyde are allowed to react in water or an alcoholic solvent (e.g., methanol or ethanol), preferably in an alcoholic solvent, particularly preferably in methanol, in the presence of an acid catalyst, preferably hydrochloric acid. In general, the ratio by mol of resorcinol to aldehyde is preferably 1:0.6 to 1.5. After completion of the reaction, crystallization is performed slowly. For example, when methanol is employed as a reaction solvent, water is added to the reaction mixture after reaction, to thereby crystallize the product. In this case, after addition of water, the reaction mixture is heated and gradually cooled again, to thereby grow the crystals slowly in order not to form higher-molecular-weight components, and water is added again, to thereby crystallize the product. Through the above procedure, a polyhydric phenol in the form of crystals containing the higher-molecular-weight components in an amount of 10% or less can be readily produced. Here, the higher-molecular-weight components are defined as components exhibiting a retention time as measured by using GPC shorter than that of the compound represented by formula (I). The thus-obtained polyhydric phenol may be recrystallized in accordance with needs.

The aldehyde employed in the reaction is at least one species selected from among C3–C10 linear or branched aldehydes. When aldehyde having less than three carbon atoms is used, the resultant 1,2-naphthoquinone-2-diazidesulfonate ester photosensitive agent exhibits poor solubility in organic solvent. Such a photosensitive agent cannot be dissolved in solvent or, even if dissolved, precipitation occurs with the elapse of time. When aldehyde having 11 or more carbon atoms is used, the resultant 1,2-naphthoquinone-2-diazidesulfonate ester photosensitive agent imparts poor sensitivity to a photoresist, and such aldehyde is not preferred. From this point of view, the aldehyde is preferably at least one species selected from among C5–C7 aldehydes.

The polyhydric phenol predominantly containing a compound represented by formula (I) contains the higher-molecular-weight components exhibiting a retention time as measured by using GPC (gel permeation chromatography) shorter than that of the compound represented by formula (I) in an amount of 10% or less, preferably 5% or less. The polyhydric phenol preferably contains substantially no lower-molecular-weight components. Thus, the polyhydric phenol predominantly containing a compound represented by formula (I) preferably has a purity (i.e., formula (I) compound content) of 90% or more, more preferably 95% or more. When the purity is less than 90%, the resultant 1,2-naphthoquinone-2-diazidesulfonate ester photosensitive agent exhibits poor solubility in organic solvent. Such a photosensitive agent cannot be dissolved in solvent or, even if dissolved, precipitation occurs with the elapse of time. Thus, the photosensitive agent cannot be used in a photoresist in combination with an alkali-soluble resin such as a novolak resin. A purity of the precipitated crystals less than 90% can be enhanced to be 90% or more through recrystallization or a similar treatment.

The GPC measurement is performed under the following conditions:

Column: Shodex GPC KF-802×1+KF-801×3

Column temperature: 40° C.

Detection wavelength: 254 nm

Eluant: THF

Flow rate of Eluant: 1.0 mL/min

The polyhydric phenol predominantly containing a compound represented by formula (I) does not substantially show an absorption at i-line (365 nm) and therefore, is particularly suitable for a raw material for producing a photosensitive agent employed in a photoresist for exposure to i-line.

The aforementioned polyhydric phenol predominantly containing the compound represented by formula (I) is reacted with 1,2-naphthoquinone-2-diazidesulfonyl chloride in the presence of a neutralizing agent, to thereby readily yield a 1,2-naphthoquinone-2-diazidesulfonate ester photosensitive agent predominantly containing a compound represented by formula (II):

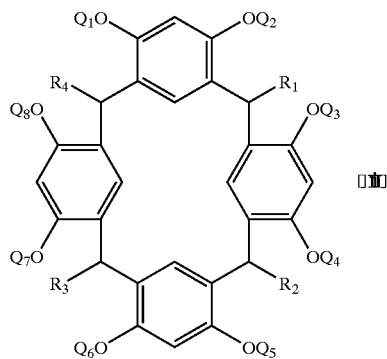

wherein each of at least two of $Q_1$, $Q_2$, $Q_3$, $Q_4$, $Q_5$, $Q_6$, $Q_7$, and $Q_8$, which are independent of one another, represents a 1,2-naphthoquinone-2-diazidesulfonyl group, and the remaining group or groups represent hydrogen; $R_1$, $R_2$, $R_3$, and $R_4$ have the same meanings as described in relation to formula (I).

The 1,2-naphthoquinone-2-diazidesulfonyl chloride is at least one species selected from among 1,2-naphthoquinone-2-diazide-4-sulfonyl chloride, 1,2-naphthoquinone-2-diazide-5-sulfonyl chloride, and 1,2-naphthoquinone-2-diazide-6-sulfonyl chloride. Of these, 1,2-naphthoquinone-2-diazide-5-sulfonyl chloride is preferably used from a viewpoint of cost thereof.

Upon reaction of 1,2-naphthoquinone-2-diazide-sulfonyl chloride in the presence of a neutralizing agent, at least one species selected from among alkylsulfonyl chloride, arylsulfonyl chloride, and aralkylsulfonyl chloride may be reacted simultaneously, before, or after the above reaction in accordance with needs.

Reaction of 1,2-naphthoquinone-2-diazidesulfonyl chloride and the polyhydric phenol predominantly containing a compound represented by formula (I) is generally carried out in an organic solvent in the presence of a neutralizing agent, the organic solvent being at least one species selected from among acetone, methyl ethyl ketone, dioxane, tetrahydrofuran, 1,3-dioxolane, γ-butyrolactone, propylene carbonate, N-methylpyrrolidone, and similar compounds. The neutralizing agent is preferably an organic amine. Examples of the organic amine include ethylamine, diethylamine, triethylamine, diisopropylamine, tripropylamine, triisobutylamine, triethanolamine, monomethyldicyclohexylamine, N-methylpiperidine, N-methylmorpholine, N-methylpyrrolidine, 1,4-dimethylpiperazine, pyridine, N,N-dimethylaniline, and N,N-dimethylaminopyridine.

Generally, the reaction involves dissolving the polyphenolic compound and 1,2-naphthoquinone-2-diazidesulfonyl chloride in an organic solvent, followed by adding an organic amine or a solution of an organic amine in solvent. Alternatively, the reaction involves dissolving the polyphenolic compound and an organic amine in an organic solvent, followed by adding 1,2-naphthoquinone-2-diazidesulfonyl chloride or a solution of 1,2-naphthoquinone-2-diazidesulfonyl chloride in solvent. Subsequently, the reaction mixture undergoes condensation reaction by stirring for 10 minutes to five hours. The above addition or the subsequent condensation reaction is performed at −10° C. to 50° C., preferably 10° C. to 40° C., for about 10 minutes to about three hours.

The amount of 1,2-naphthoquinone-2-diazidesulfonyl chloride is used in reaction with the polyhydric phenol preferably in an amount of 3 to 8 mol based on 1 mol of the polyhydric phenol, more preferably 5 to 7 mol. When the amount is less than 3 mol, a photoresist containing the resultant photosensitive agent used in combination with an alkali-soluble resin has poor contrast, whereas when the amount of in excess of 8 mol, unreacted 1,2-naphthoquinone-2-diazidesulfonyl chloride tends to remain, and the residual sulfonyl chloride decomposes thereafter to generate undesired hydrogen choaride. The neutralizing agent is generally used in an amount of 1.0 to 1.5 mol based on 1 mol of 1,2-naphthoquinone-2-diazidesulfonyl chloride, preferably 1.05 to 1.2 mol. When the amount is less than 1.0 mol, 1,2-naphthoquinone-2-diazidesulfonyl chloride tends to remain, whereas when the amount is in excess of 1.5 mol, a 1,2-quinonediazide group tends to be decomposed by the excessive neutralizing agent. The solvent is used in an amount 2 to 10 times the weight of the sum of 1,2-naphthoquinone-2-diazidesulfonyl chloride and the polyphenolic compound, preferably 3 to 5 times. When the amount is less than twice, reaction components fail to be dissolved, and storage stability of a composition containing the solvent is deteriorated, whereas when the amount is in excess of 10 times, the amount of water for causing re-precipitation increases, thereby increasing cost.

The thus-formed reaction mixture is poured into a poor solvent (e.g., water, methanol) with respect to the formed photosensitive agent, to thereby precipitate a 1,2-naphthoquinone-2-diazidesulfonate ester photosensitive agent. The thus-precipitated a 1,2-naphthoquinone-2-diazidesulfonate ester photosensitive agent is separated through filtration, washed with pure water, a diluted aqueous acid solution, or a mixture thereof with a solvent such as methanol, and dried, to thereby yield a 1,2-naphthoquinone-2-diazidesulfonate ester photosensitive agent of interest. However, since washing must be repeated in order to remove impurities such as a hydrohalide salt, a hydrohalide salt of the neutralizing agent precipitated during reaction is preferably removed through filtration, and the filtrate is poured into pure water or a similar solvent. More preferably, an acid is added to the reaction mixture after completion of reaction, to thereby acidify the reaction mixture. The formed a hydrohalide salt of the neutralizing agent is removed through filtration, and the filtrate is poured into pure water. The acid is added, after reaction, in such an amount that the ratio of (amount (mol) of 1,2-naphthoquinone-2-diazidesulfonyl chloride+amount (mol) of added acid)/(amount (mol) of neutralizing agent) falls within a range of 1.01 to 1.3. When the ratio is less than 1.01, the effect of the added acid is poor, whereas when the ratio is in excess of 1.3, impurities are incorporated in large amount into the precipitated photosensitive agent, thereby increasing washing load. Either inorganic acid or organic acid may be used. Generally, the filtrate obtained through filtration is poured into pure water, to thereby cause re-precipitation, and the thus-formed precipitates are removed through filtration again. When pure water is used, filtration is sometimes difficult. Therefore, the filtrate is preferably poured into a dilute aqueous acid solution so as to facilitate filtration. The acid added for acidifying pure water is preferably a volatile acid; e.g., hydrohalogenic acid or acetic acid. The dilute aqueous acid solution has a concentration of 0.02 N to 0.5 N. Pure water or the dilute aqueous acid solution is used in an amount 2 to 10 times the weight of the solvent used, preferably 3 to 6 times.

The re-precipitated photosensitive agent is removed through filtration, washed with pure water or a diluted aqueous acid solution, and dried, to thereby yield a 1,2-naphthoquinone-2-diazidesulfonate ester photosensitive agent of interest.

Japanese Patent Application Laid-Open (kokai) No. 9-77736 and No. 2002-207291 disclose an alternative method. Specifically, reaction is performed in an organic solvent which is separated from water, and the reaction products is washed with water, to thereby yield a 1,2-naphthoquinone-2-diazidesulfonate ester photosensitive agent in the form of a solution in organic solvent.

When the 1,2-naphthoquinone-2-diazidesulfonate ester photosensitive agent of the present invention and an alkaline-soluble resin are employed, a suitable photoresist composition can be produced.

The photoresist composition of the present invention contains any of the aforementioned 1,2-naphthoquinone-2-diazidesulfonate ester photosensitive agents. The photosensitive agents may be used singly or in combination of two or more species.

Other 1,2-naphthoquinone-2-diazidesulfonate ester photosensitive agents falling outside the present invention may also be used in accordance with needs without deviating the purpose of the present invention.

Examples of the alkali-soluble resins employed in the present invention include novolak resin, polyvinylphenol and derivatives thereof, styrene-maleic anhydride copolymer, poly(vinyl hydroxybenzoate), and carboxyl-group-containing methacrylic acid resins.

Examples of preferred resins include novolak resins. These novolak resins can be produced through polycondensation of a mono-, di-, or tri-alkylphenol and an aldehyde such as a monoaldehyde compound or a bisaldehyde compound.

Examples of the above phenols include o-cresol, m-cresol, p-cresol, 2,3-xylenol, 2,5-xylenol, 3,4-xylenol, 3,5-xylenol, 2,3,5-trimethylphenol, and 3,4,5-trimethylphenol. Of these, o-cresol, m-cresol, p-cresol, 2,3-xylenol, 2,5-xylenol, 3,4-xylenol, 3,5-xylenol, and 2,3,5-trimethylphenol are particularly preferred. These phenols may be used singly or in combination of two or more species.

Examples of the aldehyde polycondensed with the phenols include formaldehyde, trioxane, paraformaldehyde, benzaldehyde, acetaldehyde, propylaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-methylbenzaldehyde, m-methylbenzaldehyde, p-methylbenzaldehyde, p-ethylbenzaldehyde, p-n-butylbenzaldehyde, and furfural. Of these, formaldehyde is particularly preferred.

Polycondensation of the phenols and the aldehydes is generally performed in the presence of an acid catalyst. Examples include hydrochloric acid, nitric acid, sulfuric acid, formic acid, oxalic acid, acetic acid, and toluenesulfonic acid.

According to the present invention, the 1,2-naphthoquinone-2-diazidesulfonate ester photosensitive agent is used in an amount of 5 to 100 parts by weight based on 100 parts by weight of the alkali-soluble resin, preferably 20 to 70 parts by weight. When the amount of the photosensitive agent is less than 5 parts by weight, the resultant photoresist exhibits poor film fixation, whereas when the amount is in excess of 100 parts by weight, sensitivity decreases.

The photoresist composition of the present invention may further contain, in accordance with needs, additives such as a sensitizer and a surfactant.

In addition, the photoresist composition of the present invention may contain a dye or a pigment in order to visualize a latent image formed in an irradiated portion of the photoresist and minimize halation during irradiation. An adhesion promoter may also be added to the composition in order to improve adhesion of the composition. A storage-stabilizing agent, a deforming agent, and other additives may also be added in accordance with needs.

The photoresist composition of the present invention is prepared by dissolving the 1,2-naphthoquinone-2-diazidesulfonate ester photosensitive agent, the alkali-soluble resin, and the additives added in accordance with needs to a solvent such that the solid content of the resultant solution reaches 20 to 40 wt. %, and the solution is filtered by use of a filter having a pore size of approximately 0.2 µm.

Examples of the solvent for producing the solution include ethylene glycol monomethyl ether, ethylene glycol monoethyl ether, ethylene glycol monomethyl ether acetate, ethylene glycol monoethyl ether acetate, diethylene glycol monomethyl ether, diethylene glycol monoethyl ether, propylene glycol methyl ether acetate, propylene glycol propyl ether acetate, toluene, xylene, methyl ethyl ketone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-ethoxypropionate, ethyl 3-methoxypropionate, methyl 3-methoxy-2-methylpropionate, ethyl acetate, butyl acetate, and ethyl lactate. In addition to these solvents, high-boiling-point solvent may also be added. Examples include N-methylformamide, N,N-dimethylformamide, N-methylformanilide, N-methylacetamide, N,N-dimethylacetamide, N-methylpyrrolidone, dimethylsulfoxide, benzyl ethyl ether, dihexyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and phenyl cellosolve acetate. These solvents may be used singly or in combination of two or more species.

Formation of a resist pattern by use of the composition of the present invention is performed in the following manner. Firstly, the thus-prepared photoresist composition is applied on a substrate (e.g., silicon wafer, aluminum-coated wafer, glass substrate, or plastic substrate) through an appropriate coating method (e.g., spin coating, casting, or roller coating), to thereby form a resist film. The film is preliminary heated in accordance with needs (hereinafter the process is referred to as "pre-bake"), followed by exposure via a predetermined mask. The beams for exposure are preferably UV beams, with i-line (365 nm) being particularly preferred. The thus-exposed resist film is developed with an alkali developer, to thereby form a predetermined resist pattern.

EXAMPLES

The present invention will next be described in more detail by way of examples.

Synthesis Example 1
Synthesis of Polyhydric Phenol a Predominantly Containing a Compound Represented by Formula (I) ($R_1=R_2=R_3=R_4=C_2H_5$)

Resorcinol (132.13 g), propionaldehyde (58.08 g), and methanol (190 mL) were added to a five-neck flask equipped with a stirrer, a thermometer, a dropping funnel, a reflux condenser, and a nitrogen conduit. The mixture was stirred under nitrogen, and concentrated hydrochloric acid (52.09 g) was added dropwise thereto over about 15 minutes. Subsequently, the mixture was stirred under heating and under reflux conditions for three hours. Pure water (95 mL) was added dropwise thereto, and the mixture was cooled to 30° C. or lower. Pure water (285 mL) was further added thereto, to thereby allow crystals to precipitate. After the mixture had been cooled, the crystals that precipitated were collected through filtration, and the collected crystals were washed with pure water and dried in vacuum, to thereby yield 105.12 g of crystals. The purity of the crystals was measured by using GPC, and the following results were obtained: the purity of the cyclic polyhydric phenol of interest ($R_1=R_2=R_3=R_4=C_2H_5$ in formula (I)) is 95.8%, and higher-molecular-weight substances (having shorter retention time than that of the compound represented by formula (I)) and lower-molecular-weight substances (having longer retention time than that of the compound represented by formula (I)) are contained in amounts of 3.6% and 0.6%, respectively. The thus-obtained GPC chart is shown in FIG. 1.

Synthesis Example 2
Synthesis of Polyhydric Phenol b Predominantly Containing a Compound Represented by Formula (I) ($R_1=R_2=R_3=R_4=n-C_4H_9$)

Resorcinol (132.13 g), n-valeraldehyde (86.13 g), and methanol (250 mL) were added to a reactor similar to that employed in Synthesis Example 1. The mixture was stirred under nitrogen, and concentrated hydrochloric acid (52.09 g) was added dropwise thereto over about 15 minutes. Subsequently, the mixture was stirred under heating and under reflux conditions for three hours. Pure water (200 mL) was added dropwise thereto, and the mixture was cooled to 30° C. or lower. Pure water (285 mL) was further added thereto, to thereby allow crystals to precipitate. After the mixture had been cooled, the crystals that precipitated were collected through filtration, and the collected crystals were washed with pure water and dried in vacuum, to thereby yield 142.58 g of crystals. The purity of the crystals was measured by using GPC, and the following results were obtained: the purity of the cyclic polyhydric phenol of interest ($R_1=R_2=R_3=R_4=n-C_4H_9$ in formula (I)) is 96.1%, and higher-molecular-weight substances (having shorter retention time than that of the compound represented by formula (I)) and lower-molecular-weight substances (having longer retention time than that of the compound represented by formula (I)) are contained in amounts of 2.9% and 1.0%, respectively.

Synthesis Example 3
Synthesis of Polyhydric Phenol c Predominantly Containing a Compound Represented by Formula (I) ($R_1=R_2=R_3=R_4=n-C_6H_{13}$)

Resorcinol (165.17 g), n-heptanal (114.18 g), and methanol (1,300 mL) were added to a reactor similar to that employed in Synthesis Example 1. The mixture was stirred under nitrogen, and concentrated hydrochloric acid (66.21 g) was added dropwise thereto over about 15 minutes. Subsequently, the mixture was stirred under heating and under reflux conditions for three hours. Pure water (230 mL) was added dropwise thereto, and the mixture was cooled to 30° C. or lower. Pure water (180 mL) was further added thereto, to thereby allow crystals to precipitate. After the mixture had been cooled, the crystals that precipitated were collected through filtration, and the collected crystals were washed with a 50% aqueous methanol solution and dried in vacuum, to thereby yield 154.71 g of crystals. The purity of the crystals was measured by using GPC, and the following results were obtained: the purity of the cyclic polyhydric phenol of interest ($R_1=R_2=R_3=R_4=n-C_6H_{13}$ in formula (I)) is 99.3%, and higher-molecular-weight substances (having shorter retention time than that of the compound represented by formula (I)) and lower-molecular-weight substances (having longer retention time than that of the compound represented by formula (I)) are contained in amounts of 0.1% and 0.6%, respectively.

Synthesis Example 4
Synthesis of Polyhydric Phenol d Predominantly Containing a Compound Represented by Formula (I) ($R_1=R_2=R_3=R_4=$ n-$C_6H_{13}$)

Resorcinol (165.17 g), n-heptanal (114.18 g), and methanol (1,200 mL) were added to a reactor similar to that employed in Synthesis Example 1. The mixture was stirred under nitrogen, and concentrated hydrochloric acid (66.21 g) was added dropwise thereto over about 15 minutes. Subsequently, the mixture was stirred under heating and under reflux conditions for three hours. Pure water (400 mL) was added dropwise thereto. After the mixture had been cooled, crystals that precipitated were collected through filtration, and the collected crystals were washed with a 50% aqueous methanol solution and dried in vacuum, to thereby yield 156.10 g of crystals. The purity of the crystals was measured by using GPC, and the following results were obtained: the purity of the cyclic polyhydric phenol of interest ($R_1=R_2=R_3=R_4$=n-$C_6H_{13}$ in formula (I)) is 92.1%, and higher-molecular-weight substances (having shorter retention time than that of the compound represented by formula (I)) and lower-molecular-weight substances (having longer retention time than that of the compound represented by formula (I)) are contained in amounts of 7.1% and 0.8%, respectively.

Synthesis Example 5
Synthesis of Polyhydric Phenol e Predominantly Containing a Compound Represented by Formula (I) ($R_1=R_2=R_3=R_4=$ n-$C_8H_{17}$)

Resorcinol (165.17 g), n-nonanal (142.248 g), and methanol (1,500 mL) were added to a reactor similar to that employed in Synthesis Example 1. The mixture was stirred under nitrogen, and concentrated hydrochloric acid (72.84 g) was added dropwise thereto over about 15 minutes. Subsequently, the mixture was stirred under heating and under reflux conditions for three hours. Pure water (250 mL) was added dropwise thereto, and the mixture was cooled to 30° C. or lower. Pure water (180 mL) was further added thereto, to thereby allow crystals to precipitate. After the mixture had been cooled, the crystals that precipitated were collected through filtration, and the collected crystals were washed with a 50% aqueous methanol solution and dried in vacuum, to thereby yield 168.60 g of crystals. The purity of the crystals was measured by using GPC, and the following results were obtained: the purity of the cyclic polyhydric phenol of interest ($R_1=R_2=R_3=R_4$=n-$C_8H_{17}$ in formula (I)) is 99.0%, and higher-molecular-weight substances (having shorter retention time than that of the compound represented by formula (I)) and lower-molecular-weight substances (having longer retention time than that of the compound represented by formula (I)) are contained in amounts of 0.5% and 0.5%, respectively.

Synthesis Comparative Example 1
Synthesis of Polyhydric Phenol f Predominantly Containing a Compound Represented by Formula (I) ($R_1=R_2=R_3=R_4=$ $CH_3$)

Resorcinol (124.14 g), 80% acetaldehyde (66.08 g), and methanol (150 mL) were added to a reactor similar to that employed in Synthesis Example 1. The mixture was stirred under nitrogen, and concentrated hydrochloric acid (52.09 g) was added dropwise thereto over about 15 minutes. Subsequently, the mixture was stirred under heating and under reflux conditions for three hours. Pure water (500 mL) was added dropwise thereto. After the mixture had been cooled, crystals that precipitated were collected through filtration, and the collected crystals were washed with pure water. Thereafter, the washed crystals were recrystallized from water-methanol, and the resultant crystals were dried in vacuum, to thereby yield 110.95 g of crystals. The purity of the crystals was measured by using GPC, and the following results were obtained: the purity of the cyclic polyhydric phenol of interest ($R_1=R_2=R_3=R_4=CH_3$ in formula (I)) is 95.1%, and higher-molecular-weight substances (having shorter retention time than that of the compound represented by formula (I)) and lower-molecular-weight substances (having longer retention time than that of the compound represented by formula (I)) are contained in amounts of 4.7% and 0.2%, respectively.

Synthesis Comparative Example 2
Synthesis of Polyhydric Phenol g Predominantly Containing a Compound Represented by Formula (I) ($R^1=R_2=R_3=R_4=$ n-$C_4H_9$)

Resorcinol (110.11 g), n-valeraldehyde (86.13 g), and methanol (200 mL) were added to a reactor similar to that employed in Synthesis Example 1. The mixture was stirred under nitrogen, and concentrated hydrochloric acid (52.09 g) was added dropwise thereto over about 15 minutes. Subsequently, the mixture was stirred under heating and under reflux conditions for three hours. Pure water (700 mL) was added dropwise thereto. After the mixture had been cooled, crystals that precipitated were collected through filtration, and the collected crystals were washed with pure water and dried in vacuum, to thereby yield 153.64 g of crystals. The purity of the crystals was measured by using GPC, and the following results were obtained: the purity of the cyclic polyhydric phenol of interest ($R_1=R_2=R_3=R_4$=n-$C_4H_9$ in formula (I)) is 86.2%, and higher-molecular-weight substances (having shorter retention time than that of the compound represented by formula (I)) and lower-molecular-weight substances (having longer retention time than that of the compound represented by formula (I)) are contained in amounts of 12.7% and 1.1%, respectively.

Synthesis Comparative Example 3
Synthesis of Polyhydric Phenol h Predominantly Containing a Compound Represented by Formula (I) ($R_1=R_2=R_3=R_4=$ n-$C_{11}H_{23}$)

Resorcinol (132.13 g), n-dodecanal (184.32 g), and methanol (1,500 mL) were added to a reactor similar to that employed in Synthesis Example 1. The mixture was stirred under nitrogen, and concentrated hydrochloric acid (72.84 g) was added dropwise thereto over about 15 minutes. Subsequently, the mixture was stirred under heating and under reflux conditions for three hours. Pure water (250 mL) was added dropwise thereto, and the mixture was cooled to 30° C. or lower. Pure water (180 mL) was further added thereto, to thereby allow crystals to precipitate. After the mixture had been cooled, the crystals that precipitated were collected through filtration, and the collected crystals were washed with a 50% aqueous methanol solution and dried in vacuum, to thereby yield 204.02 g of crystals. The purity of the crystals was measured by using GPC, and the following results were obtained: the purity of the cyclic polyhydric phenol of interest ($R_1=R_2=R_3=R_4$=n-$C_{11}H_{23}$ in formula (I)) is 96.1%, and higher-molecular-weight substances (having shorter retention time than that of the compound represented by formula (I)) and lower-molecular-weight substances (having longer retention time than that of the compound represented by formula (I)) are contained in amounts of 3.0% and 0.9%, respectively.

Example 1
Synthesis Example of Photosensitive Agent A

Polyhydric phenol a (12.01 g, 0.02 mol), 1,2-naphthoquinonediazide-5-sulfonyl chloride (26.87 g, 0.10 mol), γ-butyrolactone (40 g), and acetone (150 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 33.2 g of 1,2-naphthoquinone-2-diazidesulfonate ester photosensitive agent A.

Example 2
Synthesis Example of Photosensitive Agent B

Polyhydric phenol b (14.26 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (720 g). The resultant precipitates were separated through filtration, washed with water, and dried, to thereby yield 35.3 g of 1,2-naphthoquinone-2-diazidesulfonate ester photosensitive agent B.

Example 3
Synthesis Example of Photosensitive Agent C

Polyhydric phenol b (23.74 g, 0.033 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (720 g). The resultant precipitates were separated through filtration, washed with water, and dried, to thereby yield 44.3 g of 1,2-naphthoquinone-2-diazidesulfonate ester photosensitive agent C.

Example 4
Synthesis Example of Photosensitive Agent D

Polyhydric phenol b (35.65 g, 0.05 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (720 g). The resultant precipitates were separated through filtration, washed with water, and dried, to thereby yield 56.4 g of 1,2-naphthoquinone-2-diazidesulfonate ester photosensitive agent D.

Example 5
Synthesis Example of Photosensitive Agent E

Polyhydric phenol c (16.50 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 35.3 g of 1,2-naphthoquinone-2-diazidesulfonate ester photosensitive agent E.

Example 6
Synthesis Example of Photosensitive Agent F

Polyhydric phenol c (11.78 g, 0.0143 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 32.6 g of 1,2-naphthoquinone-2-diazidesulfonate ester photosensitive agent F.

Example 7
Synthesis Example of Photosensitive Agent G

Polyhydric phenol d (16.50 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 35.8 g of 1,2-naphthoquinone-2-diazidesulfonate ester photosensitive agent G.

Example 8
Synthesis Example of Photosensitive Agent H

Polyhydric phenol e (18.75 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 40.1 g of 1,2-naphthoquinone-2-diazidesulfonate ester photosensitive agent H.

Comparative Example 1
Synthesis Example of Photosensitive Agent I

Polyhydric phenol f (10.89 g, 0.02 mol), 1,2-naphthoquinonediazide-5-sulfonyl chloride (26.87 g, 0.10 mol), γ-butyrolactone (40 g), and acetone (150 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 31.7 g of 1,2-naphthoquinone-2-diazidesulfonate ester photosensitive agent I.

Comparative Example 2
Synthesis Example of Photosensitive Agent J

Polyhydric phenol g (14.26 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (720 g). The resultant precipitates were separated through filtration, washed with water, and dried, to thereby yield 36.1 g of 1,2-naphthoquinone-2-diazidesulfonate ester photosensitive agent J.

Comparative Example 3
Synthesis Example of Photosensitive Agent K

Polyhydric phenol h (22.11 g, 0.02 mol), 1,2-naphthoquinonediazide-5-sulfonyl chloride (26.87 g, 0.10 mol), and acetone (210 g) were placed in a three-neck flask and mixed, to thereby yield a uniform solution. To the solution, a mixture of triethylamine/acetone (11.4 g/11.4 g) was added dropwise at 30 to 35° C. over 60 minutes. The resultant mixture was stirred at 30 to 35° C. for 40 minutes, followed by neutralization with concentrated hydrochloric acid (2.1 g). The precipitated triethylamine hydrochloride was removed through filtration, and the reaction mixture (filtrate) was poured into pure water (670 g). The resultant precipitates were separated through filtration, washed with water, and dried, to thereby yield 44.2 g of 1,2-naphthoquinone-2-diazidesulfonate ester photosensitive agent K.

Synthesis Example of Novolak Resin m-Cresol (50 g), p-cresol (25 g), 2,5-xylenol (28 g), a 37% aqueous formalin solution (53 g), and oxalic acid (0.15 g) were placed in a three-necked flask. Under stirring, the resultant mixture was heated to 100° C. and allowed to react for 14 hours. Subsequently, the mixture was heated to 200° C., and the pressure was gradually reduced, to thereby evaporate water, unreacted monomers, formaldehyde, oxalic acid, and other substances. Thereafter, the resultant crude novolak resin was separated from methanol/water, and the resultant resin was dried under heating and reduced pressure for 24 hours, to thereby yield a purified novolak resin (alkali-soluble). The thus-obtained novolak resin was found to have a weight-average molecular weight of 6,400 as reduced to polystyrene.

Test Example 1
Solubility of Photosensitive Agents

Each of the photosensitive agents synthesized in the above Examples and Comparative Examples was evaluated in terms of solubility in ethyl lactate and in propylene glycol methyl ether acetate. The solubility was investigated at 10 wt. % and evaluated using the following criteria.

◯: completely dissolved

Δ: once dissolved but later precipitated

×: not dissolved

The results are shown in Table 1.

TABLE 1

| | | photosensitive agent | | | Solubility | |
|---|---|---|---|---|---|---|
| | | Starting polyhydric phenol | | | | |
| | Types | $R_1$–$R_4$ | Higher-molecular-weight components | Mole ratio*1 | Ethyl lactate | Propylene glycol methyl ether acetate |
| Ex. 1 | Photosensitive agent A | $C_2$ | 3.6% | 1:5 | ◯ | Δ |
| Ex. 2 | Photosensitive agent B | $C_4$ | 2.9% | 1:5 | ◯ | ◯ |
| Ex. 3 | Photosensitive agent C | $C_4$ | 2.9% | 1:3 | ◯ | ◯ |
| Ex. 4 | Photosensitive agent D | $C_4$ | 2.9% | 1:2 | ◯ | ◯ |
| Ex. 5 | Photosensitive agent E | $C_6$ | 0.1% | 1:5 | ◯ | ◯ |
| Ex. 6 | Photosensitive agent F | $C_6$ | 0.1% | 1:7 | ◯ | ◯ |
| Ex. 7 | Photosensitive agent G | $C_6$ | 7.1% | 1:5 | ◯ | Δ |
| Ex. 8 | Photosensitive agent H | $C_8$ | 0.5% | 1:5 | ◯ | ◯ |
| Comp. Ex. 1 | Photosensitive agent I | $C_1$ | 4.7% | 1:5 | Δ | × |
| Comp. Ex. 2 | Photosensitive agent J | $C_4$ | 12.7% | 1:5 | Δ | × |

TABLE 1-continued

| | | Starting polyhydric phenol | | | Solubility | |
|---|---|---|---|---|---|---|
| | Types | $R_1$–$R_4$ | Higher-molecular-weight components | Mole ratio*1 | Ethyl lactate | Propylene glycol methyl ether acetate |
| Comp. Ex. 3 | Photosensitive agent K | $C_{11}$ | 3.0% | 1:5 | ○ | ○ |

*1 polyhydric phenol:1,2-naphthoquinone-2-diazidesulfonyl chloride

As is apparent from Table 1, photosensitive agents produced from a starting polyhydric phenol having C1 alkyl group represented by $R_1$–$R_4$ and photosensitive agents containing higher-molecular-weight components in an amount more than 10% exhibit poor solubility.

Examples 9 to 16 and Comparative Examples 4 to 6

Preparation of Photoresist Compositions From the Above Photosensitive Agents

Each of the photosensitive agents A to K was mixed with 100 parts by weight of each of novolak resins synthesized in Synthesis Example in an amount (part by weight) indicated in Table 2, and the mixture was dissolved in ethyl lactate (500 parts by weight). Fluorad FC-430 (surfactant, 0.35 parts by weight, product of 3M) was added thereto, and the mixture was applied onto a membrane filter (0.2 μm), to thereby yield a resist solution (Examples 9 to 16 and Comparative Examples 4 to 6, respectively).

Test Example 2

Storage Stability and Sensitivity of Photoresist Compositions

The solutions prepared in Examples 9 to 16 and Comparative Examples 4 to 6 were stored at 40° C. for one month. Presence or absence of precipitates was visually observed for evaluation of storage stability. Evaluation standards are as follows.

○: no precipitates
Δ: slight amount of precipitates
×: precipitates are clearly observed Each of the above resist solutions was applied to a silicon wafer which had been treated with hexamethyldisilazane by means of spin-coating so as to obtain a thickness of the dried film of 1.05 μm. The wafer was dried on a hot-plate at 110° C. for 90 seconds. The resultant resist film was exposed to i-line and developed with 2.38% aqueous tetramethylammonium hydroxide solution (temperature: 23° C., time: 90 seconds). A sensitivity curve was thus-created, based on which sensitivity was determined. The results are shown in Table 2.

TABLE 2

| | Photosensitive agent (parts by weight) | Storage stability | Sensitivity (mJ/cm²) |
|---|---|---|---|
| Ex. 9 | A(30) | Δ | 50 |
| Ex. 10 | B(23) | ○ | 70 |
| Ex. 11 | C(30) | ○ | 40 |
| Ex. 12 | D(35) | Δ | 30 |
| Ex. 13 | E(23) | ○ | 80 |
| Ex. 14 | F(20) | ○ | 85 |
| Ex. 15 | G(23) | Δ | 85 |
| Ex. 16 | H(23) | ○ | 90 |
| Comp. Ex. 4 | I(20) | × | 60 |
| Comp. Ex. 5 | J(23) | × | 75 |
| Comp. Ex. 6 | K(26) | ○ | 150 |

As is apparent from Table 2, resist compositions containing the photosensitive agents of the present invention exhibit excellent storage stability and high sensitivity.

As described hereinabove, according to the present invention, there can be provided a 1,2-naphthoquinone-2-diazidesulfonate ester photosensitive agent which has high solubility in solvent and is useful as a photosensitive agent employed in a photoresist for producing semiconductor integrated circuits, liquid crystal displays, EL displays, etc., a method for producing the photosensitive agent, and a photoresist composition containing the photosensitive agent.

What is claimed is:

1. 1,2-Naphthoquinone-2-diazidesulfonate ester photosensitive agent which is produced by reacting a polyhydric phenol with 1,2-naphthoquinone-2-diazidesulfonyl chloride in the presence of a neutralizing agent, wherein the polyhydric phenol is obtained by a condensation reaction between resorcinol and at least one aldehyde selected from C3–C10 aldehydes, and contains, as a predominant component, a compound represented by formula (I) and components exhibiting a retention time as measured by using GPC shorter than that of the compound represented by formula (I) in an amount of 10% or less:

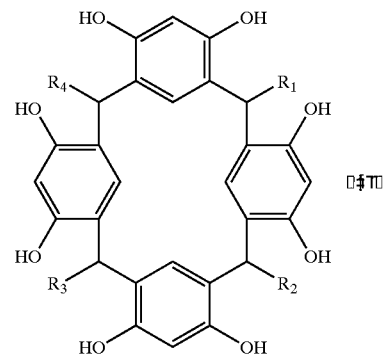

wherein each of $R_1$, $R_2$, $R_3$, and $R_4$ represents a C2–C9 alkyl group.

2. 1,2-Naphthoquinone-2-diazidesulfonate ester photosensitive agent according to claim 1, wherein the polyhydric phenol containing the compound represented by formula (I) as a predominant component contains, in an amount of 5% or less, components exhibiting a retention time as measured by using GPC shorter than that of the compound represented by formula (I).

3. 1,2-Naphthoquinone-2-diazidesulfonate ester photosensitive agent according to claim 1, wherein each of $R_1$, $R_2$, $R_3$, and $R_4$ in formula (I) is a C4–C6 alkyl group.

4. 1,2-Naphthoquinone-2-diazidesulfonate ester photosensitive agent according to claim 1, wherein the polyhydric phenol containing the compound represented by formula (I) as a predominant component is reacted with 1,2-naphthoquinone-2-diazidesulfonyl chloride in an amount of at least 3 mol based on 1 mol of the polyhydric phenol.

5. 1,2-Naphthoquinone-2-diazidesulfonate ester photosensitive agent according to claim 1, which is incorporated into a photoresist for exposure to i-line.

6. A photoresist composition comprising a 1,2-naphthoquinone-2-diazidesulfonate ester photosensitive agent as recited in any one of claims 1 to 5 and an alkali-soluble resin.

7. A photoresist composition according to claim 6, which is employed for exposure to i-line.

8. A method for producing a 1,2-naphthoquinone-2-diazidesulfonate ester photosensitive agent comprising the steps of: obtaining a polyhydric phenol by a condensation reaction between resorcinol and at least one aldehyde selected from C3–C10 aldehydes, which the polyhydric phenol contains, as a predominant component, a compound represented by formula (I), and components exhibiting a retention time as measured by using GPC shorter than that of the compound represented by formula (I) in an amount of 10% or less:

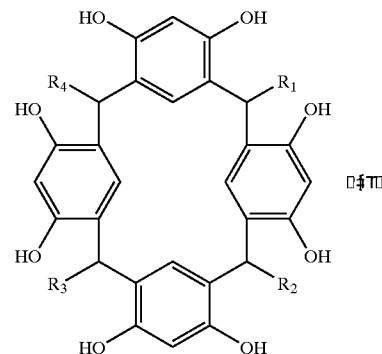

wherein each of $R_1$, $R_2$, $R_3$, and $R_4$ represents a C2–C9 alkyl group; and reacting the polyhydric phenol with 1,2-naphthoquinone-2-diazidesulfonyl chloride in the presence of a neutralizing agent.

* * * * *